US008592199B2

(12) United States Patent
Ardell

(10) Patent No.: US 8,592,199 B2
(45) Date of Patent: Nov. 26, 2013

(54) GENETIC ENCRYPTION

(76) Inventor: David H. Ardell, Catheys Vay, CA (US)

(*) Notice: Subject to any disclaimer, the term of this patent is extended or adjusted under 35 U.S.C. 154(b) by 290 days.

(21) Appl. No.: 12/811,036

(22) PCT Filed: Dec. 29, 2008

(86) PCT No.: PCT/US2008/088400
§ 371 (c)(1),
(2), (4) Date: Oct. 4, 2010

(87) PCT Pub. No.: WO2009/086497
PCT Pub. Date: Jul. 9, 2009

(65) Prior Publication Data
US 2012/0117673 A1 May 10, 2012

Related U.S. Application Data

(60) Provisional application No. 61/017,372, filed on Dec. 28, 2007.

(51) Int. Cl.
*C12N 1/21* (2006.01)
(52) U.S. Cl.
USPC .................... 435/252.33; 435/317.1; 435/488
(58) Field of Classification Search
None
See application file for complete search history.

(56) References Cited

U.S. PATENT DOCUMENTS

| | | |
|---|---|---|
| 2006/0088911 A1 | 4/2006 | Laplaza |
| 2007/0004041 A1 | 1/2007 | Church |
| 2007/0238152 A1 | 10/2007 | Wang |

OTHER PUBLICATIONS

Normanly et al., Annu. Rev. Biochem. (1989) vol. 58, pp. 1029-1049.*
Breitschopf, K. and H. J. Gross. 1994. The exchange of the discriminator base A73 for G is alone sufficient to convert human tRNA(Leu) into a serine-acceptor in vitro. Embo J 13(13): 3166-3169.
Buchan, J. R., L. S. Aucott and I. Stansfield. 2006. tRNA properties help shape codon pair preferences in open reading frames. Nucleic Acids Res 34(3): 1015-1027.
Cho, M. K., D. Magnus, A. L. Caplan and D. McGee. 1999. Policy forum: genetics. Ethical considerations in synthesizing a minimal genome. Science 286(5447): 2087, 2089-2090.
Dale, T. and O. C. Uhlenbeck. 2005. Amino acid specificity in translation. Trends Biochem Sci 30(12): 659-665.
Helm, M. 2006. Post-transcriptional nucleotide modification and alternative folding of RNA. Nucleic Acids Res 34(2): 721-733.
Hills, M. J., L. Hall, P. G. Arnison and A. G. Good. 2007. Genetic use restriction technologies (GURTs): strategies to impede transgene movement. Trends Plant Sci 12(4): 177-183.
Jager, G., R. Leipuviene, M. G. Pollard, Q. Qian and G. R. Bjork. 2004. The conserved Cys-XI-X2-Cys motif present in the TtcA protein is required for the thiolation of cytidine in position 32 of tRNA from *Salmonella enterica* serovar Typhimurium. J Bacteriol 186(3): 750-757.
Keseler, I. M., J. Collado-Vides, S. Gama-Castro, J. Ingraham, S. Paley, I. T. Paulsen, M. Peralta-Gil and P. D. Karp. 2005. EcoCyc: a comprehensive database resource for *Escherichia coli*. Nucleic Acids Res 33(Database issue): D334-337.
Lartigue, C, J. I. Glass, N. Alperovich, R. Pieper, P. P. Parmar, C. A. Hutchison, 3rd, H. O. Smith and J. C. Venter. 2007. Genome transplantation in bacteria: changing one species to another. Science 317(5838): 632-638.
Leuker, C. E. and J. F. Ernst 1994. Toxicity of a heterologous leucyl-tRNA (anticodon CAG) in the pathogen *Candida albicans*: in vivo evidence for non-standard decoding of CUG codons. Mol Gen Genet 245(2): 212-217.
Qian, Q. and G. R. Bjork. 1997. Structural requirements for the formation of 1-methylguanosine in vivo in tRNA(Pro) GGG of *Salmonella typhimurium*. J Mol Biol 266(2): 283-296.
Redlak, M., C. Andraos-Selim, R. Giege, C. Florentz and W. M. Holmes. 1997. Interaction of tRNA with tRNA (guanosine-1)methyltransferase: binding specificity determinants involve the dinucleotide G36pG37 and tertiary structure. Biochemistry 36(29): 8699- 8709.
Smith, H. O., C. A. Hutchison, 3rd, C. Pfannkoch and J. C. Venter. 2003. Generating a synthetic genome by whole genome assembly: phiX174 bacteriophage from synthetic oligonucleotides. Proc Natl Acad Sd U S A 100(26): 15440-15445.
Soma, A., R. Kumagai, K. Nishikawa and H. Himeno. 1996. The anticodon loop is a major identity determinant of *Saccharomyces cerevisiae* tRNA(Leu). J Mol Biol 263(5): 707-714.
Sugiyama, H., M, Ohkuma, Y. Masuda, S. M. Park, A. Ohta and M. Takagi. 1995. In vivo evidence for non-universal usage of the codon CUG in *Candida maltosa*. Yeast 11(1): 43-52.
Tian, J., H. Gong, N. Sheng, X. Zhou, E. Gulari, X. Gao and G. Church. 2004. Accurate multiplex gene synthesis from programmable DNA microchips. Nature 432(7020): 1050-1054.
Tsang, T. H., M. Buck and B. N. Ames. 1983. Sequence specificity of tRNA-modifying enzymes. An analysis of 258 tRNA sequences. Biochim Biophys Acta 741(2): 180-196.
Wiltschi, B. and N. Budisa. 2007. Natural history and experimental evolution of the genetic code. Appl Microbiol Biotechnol 74(4): 739-753.
Yarus, M. 1982. Translational efficiency of transfer RNA's: uses of an extended anticodon. Science 218(4573): 646-652.
Zimmer, T. and W. H. Schunck. 1995. A deviation from the universal genetic code in *Candida maltosa* and consequences for heterologous expression of cytochromes P450 52A4 and 52A5 in *Saccharomyces cerevisiae*. Yeast 11(1): 33-41.

(Continued)

*Primary Examiner* — Jim Ketter
(74) *Attorney, Agent, or Firm* — Foley & Lardner LLP; Antoinette F. Konski; Alex Y. Nie

(57) ABSTRACT

The present invention relates to a method to engineer either the genome of a genetically modified organism, other bioengineered reagent, or in vitro translation system for protein synthesis from specific protein-coding genes so that the protein-coding genes so engineered can only produce proteins with an intended structure when translated within the context of that specifically engineered GMO or in vitro translation system. It also relates to nucleic acids for use in such GMOs or translation systems.

21 Claims, 5 Drawing Sheets

(56) References Cited

OTHER PUBLICATIONS

Cello, Jeronimo, et al. 2002. Chemical Synthesis of Poliovirus cDNA: Generation of Infectious Virus in the Absence of Natural Template. Science 297:1016-1018.

Cello, J., Paul, Aniko V. and Wimmer, Eckard. 2002. Chemical Synthesis of Poliovirus cDNA: Generation of Infectious Virus in the Absence of Natural Template. Science Magazine vol. 297. 1016-1018.

Hills, M. J., L. Hall, P. G. Amison and A. G. Good. 2007. Genetic use restriction technologies (GURTs): strategies to impede transgene movement. Trends Plant Sci 12(4): 177-183.

Jager, G., R. Leipuviene, M. G. Pollard, Q. Qian and G. R. Bjork. 2004. The conserved Cys-X1-X2-Cys motif present in the TtcA protein is required for the thiolation of cytidine in position 32 of tRNA from *Salmonella enterica* serovar Typhimurium. J Bacteriol 186(3): 750-757.

\* cited by examiner

GENETIC ENCRYPTION

SEQUENCE LISTING

The instant application contains a Sequence Listing which has been submitted via EFS-Web and is hereby incorporated by reference in its entirety.

FIELD OF THE INVENTION

The present invention relates to genetic engineering, and especially genetically modified cells and organisms with a reduced risk for unintended gene transfer of engineered genes into the surrounding environment.

BACKGROUND OF THE INVENTION

One of the greatest risks associated with the biotechnological use or release into the environment of genetically modified organisms (GMOs), cell-lines or viruses (henceforth "bioengineered reagents") is unintended transfer of engineered genes into natural populations by hybridization or horizontal gene transfer. There is thus a need in the art for improved methods for reducing or completely eliminating unintended transfer of engineered genes into natural populations.

SUMMARY OF THE INVENTION

This risk would be circumvented if these bioengineered reagents could be engineered so that their genes do not produce functional proteins in natural genetic backgrounds or even other engineered backgrounds. It may also be desirable to restrict the production of proteins from genes only when those genes are combined with a specific in vitro translation system.

The present invention addresses the above mentioned needs by providing a method to engineer either the genome of a GMO, other bioengineered reagent, or in vitro translation system for protein synthesis from specific protein-coding genes so that the protein-coding genes so engineered can only produce proteins with an intended structure when translated within the context of that specifically engineered GMO or in vitro translation system. The fully correct information of those protein-coding genes so engineered is "locked" and can only be expressed in a specific genetic background or among a specific in vitro reagent mixture that contains the correct "keys." A suitable way to describe protein-coding genetic information altered in this way is that it is "encrypted."

The encryption referred to here is a kind of substitution cipher. That is, protein-coding information is rewritten so that codons code for different amino acids than they do in otherwise natural or artificial genetic code. The intention of the design is not to obfuscate encoded protein information of a gene, but rather to make the value of that information— synthesis of functional proteins and possibly overall organismal fitness—dependent on artificially constructed traits of the translational apparatus that cannot themselves be easily acquired by other organisms. This kind of genetic encryption is therefore a genetic use restriction technology (GURT) (Hills, M. J. et al. 2007) that has potential application in restricting the movement of genes between synthetic organisms or bioengineering reactors into natural populations. It may also confer viral resistance to said synthetic organisms or bioengineering reactors.

The invention thus relates to protein encoding genes that are encrypted and also to tRNAs that can translate such encrypted genes into sense proteins. In the following, references to position numbers or base-pairs use the standard way to refer to nucleotide positions of tRNAs as given for example in [Laslett, 2004 #75] and illustrated partly in FIG. 1.

In a first aspect, the invention relates to a chimaeric tRNA molecule having an anticodon matching a codon, according to the standard genetic code of an organism, wherein said chimaeric tRNA is charged with an amino acid that is not coded for by said codon in said standard genetic code, when said chimaeric tRNA is expressed in said organism.

In one embodiment of this aspect, said chimaeric tRNA is charged with an amino acid that is coded for by said codon in a predefined alternative genetic code, when said chimaeric tRNA is expressed in said organism.

In a further embodiment, said chimaeric tRNA has a nucleotide sequence from position 1-26:33 and 37:44-76 corresponding to a first gene encoding a first tRNA and an intermediate nucleotide sequence from position 27:34-36:43 corresponding to a second gene encoding a second tRNA. The expression "nucleotide sequence from position X-Y:Z" shall mean that the nucleotide sequence starts at position X and ends at any of the positions Y-Z. The expression "nucleotide sequence from position X:Y-Z" shall mean that the nucleotide sequence starts at any of positions X-Y and ends at position Z. The expression "nucleotide sequence from position X:Y-Z:W" shall mean that the nucleotide sequence starts at any of positions X-Y and ends at any of positions Z-W.

In a further embodiment, said chimaeric tRNA has a nucleotide sequence from position 1-26 and 44-76 corresponding to a first gene encoding a first tRNA and an intermediate nucleotide sequence from position 27-36 corresponding to a second gene encoding a second tRNA.

In a further embodiment, the invention relates to a chimaeric tRNA wherein said codon encodes leucine in said predefined alternative genetic code and serine in said standard genetic code and/or wherein said codon encodes serine in said predefined alternative genetic code and leucine in said standard genetic code.

In a further embodiment, the invention relates to a chimaeric tRNA wherein said codon encodes leucine in said predefined alternative genetic code and alanine in said standard genetic code and/or wherein said codon encodes alanine in said predefined alternative genetic code and leucine in said standard genetic code.

In a further embodiment, the invention relates to a chimaeric tRNA wherein said codon encodes alanine in said predefined alternative genetic code and serine in said standard genetic code and/or wherein said codon encodes serine in said predefined alternative genetic code and alanine in said standard genetic code.

In a further embodiment of this aspect, the invention relates to nucleic acid encoding such a chimaeric tRNA molecule, optionally further comprising regulatory sequences of said first gene templating a first tRNA.

In a second aspect, the invention relates to encrypted protein-encoding nucleic acids and to a method for obtaining such encrypted protein-encoding nucleic acids.

In a first embodiment of this aspect, the invention relates to a method for designing the nucleotide sequence of a nucleic acid molecule, comprising the steps
  a. obtaining an original nucleotide sequence encoding an original protein from an organism in a standard genetic code in said organism
  b. changing all occurrences of a codon encoding a specific amino acid to an alternative codon, according to a predefined alternative genetic code;

c. repeating step b any number of times until the designed nucleotide sequence encodes the original protein in the alternative genetic code.

Optionally, in step b, all codons encoding a specific amino acid are changed.

In a further embodiment, this aspect relates to a method for producing a nucleic acid molecule comprising the steps
a. designing a nucleotide sequence according to the method of the above embodiment; and
b. producing a nucleic acid molecule having the nucleotide sequence obtained in step a.

This aspect also relates to a nucleic acid molecule produced with the above method.

In a further aspect, the invention relates to a genetically modified cell or in vitro translation system comprising a chimaeric tRNA molecule according to the first aspect and a nucleic acid molecule according to the second aspect, wherein the alternative genetic code is the same.

In one embodiment of this aspect, said alternative genetic code is derived from said standard genetic code by letting at least one first codon, coding for a first amino acid in said standard genetic code, code for a second amino acid in said alternative genetic code, and letting a codon coding for said second amino acid in said standard genetic code, code for said first amino acid in said alternative genetic code. This embodiment corresponds to a partial codon swapping.

In a further embodiment, said alternative genetic code is derived from said standard genetic code by letting all codons, coding for a first amino acid in said standard genetic code, code for a second amino acid in said alternative genetic code, and letting all codons coding for said second amino acid in said standard genetic code, code for said first amino acid in said alternative genetic code.

This embodiment corresponds to a total codon swapping.

In a further embodiment, the alternative genetic code is derived from said standard genetic code by rotation of codons, e.g. Ser->Leu->Ala->Ser. Either all codons decoding an amino acid are exchanged, alternatively only a part of the codons are exchanged.

This embodiment can be generically expressed as a cell according to this aspect, wherein said alternative genetic code is derived from said standard genetic code by letting at least one first codon ($c_1$), coding for a first amino acid ($aa_1$) in said standard genetic code, code for a second amino acid ($aa_2$) in said alternative genetic code, and, analogously, letting an n:th codon $c_n$, wherein 1<n<N, coding for an n:th amino acid $aa_n$ in said standard genetic code, code for a n+1:th amino acid in said alternative genetic code, and letting the N:th codon $c_N$ code for $aa_1$ in said alternative genetic code.

This embodiment includes the embodiment wherein said alternative genetic code is derived from said standard genetic code by letting all codons, coding for a first amino acid ($aa_1$) in said standard genetic code, code for a second amino acid ($aa_2$) in said alternative genetic code, and, analogously, letting all codons coding for an n:th amino acid $aa_n$, wherein 1<n<N, in said standard genetic code, code for an n+1:th amino acid in said alternative genetic code, and letting all codons coding for $aa_N$ in said standard genetic code, code for $aa_1$ in said alternative genetic code.

The invention further relates to multicellular organisms comprising a cell according to the above aspect, such as fungi, plants and non-human animals.

In a further aspect, the invention relates to a virus comprising an encrypted nucleic acid.

In a further aspect, the invention relates to a method for producing a genetically modified cell, comprising the steps synthesizing a genome incorporating at least one nucleic acid encoding a chimaeric tRNA molecule according to the above first aspect and at least one nucleic acid according to the above second aspect; and
transplanting said genome to said cell.

In a further aspect, the invention relates to a method for producing a genetically modified virus, comprising the steps
synthesizing a genome incorporating at least one nucleic acid according to the above second aspect; and
transplanting said genome to said virus.

The invention further relates to methods for changing an original genetic code into an alternative genetic code.

In one embodiment of this aspect the method comprises letting at least one first codon, coding for a first amino acid in said original genetic code, code for a second amino acid in said alternative genetic code, and letting a codon coding for said second amino acid in said original genetic code, code for said first amino acid in said alternative genetic code. In a further embodiment of this aspect the method comprises letting at least one first codon ($c_1$), coding for a first amino acid ($aa_1$) in said original genetic code, code for a second amino acid ($aa_2$) in said alternative genetic code, and, analogously, letting an n:th codon $c_n$, wherein 1<n<N, coding for an n:th amino acid $aa_n$ in said original genetic code, code for a n+1:th amino acid in said alternative genetic code, and letting the N:th codon $c_N$ code for $aa_1$ in said alternative genetic code.

The above mentioned aspects of the invention are further described in the detailed description and the drawings.

DETAILED DESCRIPTION OF THE INVENTION

Figure 1:
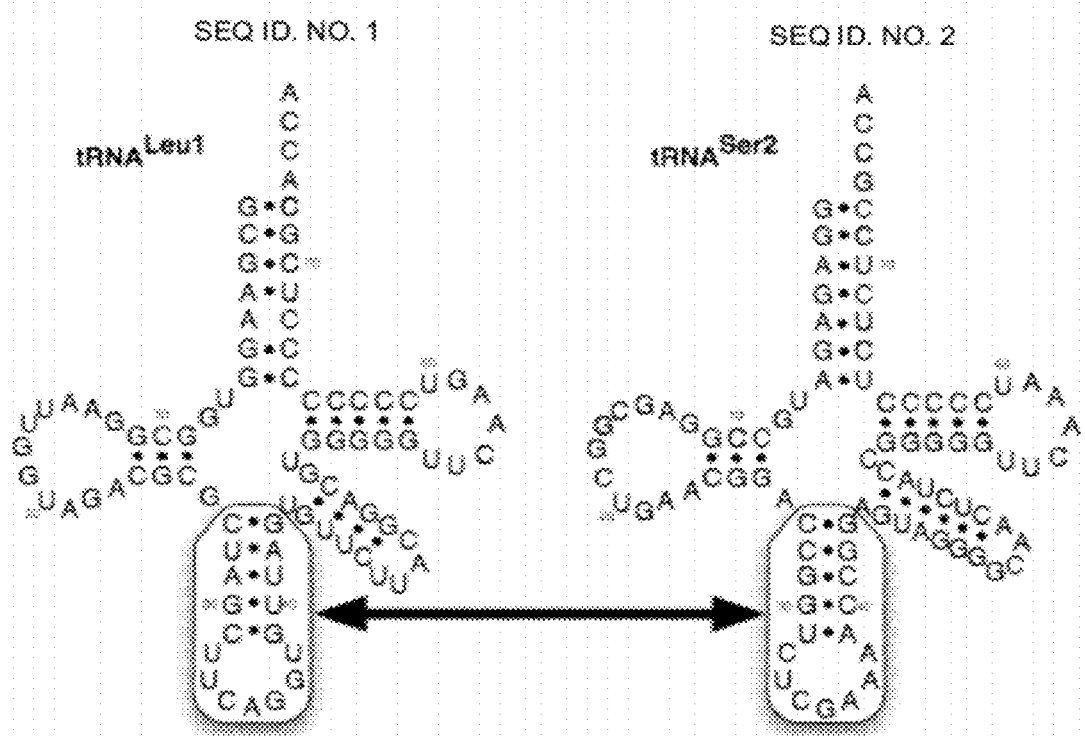
FIG. 1. Example of effect of genetic alteration to tRNA genes discussed in the text, resulting in a swap of ASLs up to an including the 27-43 base-pair. Shown here are the unmodified tRNA sequences of *E. coli* K12 tRNA-Leu1-CAG [SEQ ID NO: 1] and tRNA-Ser2-CGA [SEQ ID NO: 2] to be exchanged as in the SL4 or SL6 designs.

This invention provides feasible genetic designsto effectively achieve isolation from genetic exchange of all protein-coding genes of a GMO, biological reagent or in vitro translation system. These genetic designs all require simultaneous changes to selected tRNA genes and all protein-coding genes in a biological reagent or in vitro translation system to achieve alteration of the genetic code in that system. For example, one way all of these simultaneous genetic changes may be effected could be through fabricating a synthetic genome incorporating one or more of the designs described herein, followed by transplantation of that genome into a Genetically Modified Organisms (GMOs). Genetic encryption by the invention described here has the following properties: 1) when encrypted genes are moved into an unencrypted genetic background, the proteins produced by those encrypted genes will in almost all circumstances have a disrupted amino acid sequence and will therefore be very likely not to fold properly or function in that background; 2) when unencrypted genes are moved into an encrypted genetic background, the proteins produced by those unencrypted genes will in almost all circumstances have exactly the same disrupted amino acid sequence (the same sequence as described in property 1 above) and therefore have the same high likelihood of not folding properly or functioning; 3) any natural, altered, or completely synthetic unencrypted protein-coding gene sequence may be easily encrypted so that it will produce exactly the same (most highly probable) amino acid sequence in the specific encrypted genetic background as the original unencrypted gene would produce in an unencrypted background; 4) loss—through natural processes—of the encrypted trait in an eGMO to become unencrypted is practically impossible; and 5) acquisition of the encrypted trait from an eGMO to an unencrypted natural or synthetic organism through natural processes is practically impossible. The specific method of genetic encryption described here is therefore a genetic use restriction technology which adds value to any and all areas in which synthetic genomics holds promise.

The specific designs described here engineer changes in components of the translational apparatus to achieve a specific and functional alteration of the genetic code. This alteration exchanges the encoded amino acid meanings of multiple codons for up to three canonical amino acids, serine, leucine, and alanine. When protein-coding genes are engineered according to this altered genetic code, they are encrypted. When those genes are translated in a natural genetic background, in vitro translation system, or any other translation system that is not itself engineered correspondingly, the proteins thereby produced are very likely not to fold correctly, to be missing essential catalytic residues or both, and are therefore likely to be nonfunctional. In the context of a natural organism, the misfolded proteins produced from encrypted genes are likely to be quickly degraded. Because encrypted genes are very likely to produce nonfunctional and misfolded proteins, they themselves are very unlikely to be evolutionarily retained and gain frequency in natural populations. Genetic encryption therefore, as defined herein is a genetic use retriction technnology (GURT).

If a GMO, biological reagent such as cell-line or virus, or in vitro translation system is engineered according to the designs described here, it is called an "encrypted GMO" (eGMO), "encrypted biological reagent" or "encrypted in vitro translation system." Encypted GMOs, biological reagents or in vitro translation systems have the property that not only specific genes but all of their protein-coding genes are encrypted. If any of their protein-coding genes move into the genetic background of a natural organism, any one of them has a high likelihood of producing nonfunctional and misfolded protein. Furthermore, the encrypted GMO biological reagent or translation system is unable to acquire or translate genes from other organisms, biological reagents or translation systems that have not themselves also been encrypted in the same way. Encryption, therefore, effectively isolates all protein-coding genes between encrypted and natural systems. Finally, encryption also confers the property of resistance to natural or synthetic viruses that are not themselves accordingly encrypted.

The following problems must be solved to create an encrypted GMO, biological reagent or in vitro translation system (henceforth translation system):

Sufficient modification of its genetic code so that a gene conforming to that code would either produce nonfunctioning protein in a natural organism or be completely untranslatable.

Modification of all protein-coding genes in the translation system to conform to that genetic code.

Remediation of secondary functional and performance loss in the translation system caused by these modifications.

The first two problems may be solved by modification of the emerging technologies of synthetic genomics and genome transplantation. Briefly, the entire genome of the GMO will soon be able to be synthesized. The ability to transplant genomes into cells was recently demonstrated.

The solution to problem 1 is to swap or rotate—by genetic engineering or whole genome synthesis—the Anticodon Stem-Loops (ASL) templates of all tRNA genes in a genome or genes used to create an in vitro translation system for two or more classes of tRNAs that accept different amino acids, exchanging the codon reading specificities of the tRNAs that they template without while preserving their amino acid charging specificities. Certain tRNAs are well-documented to be charged independently of their anticodon stem-loops in most, if not all organisms—specifically, the tRNAs that accept the amino acids alanine (Ala), leucine (Leu) and serine (Ser)—although the possibility is open that this property pertains to other types of tRNAs in specific organisms or biological reagents.

The solution to problem 2 is to synthetically swap every codon of every protein-coding gene, including any modified or inserted genes in parallel to the tRNA modifications made in step 1.

There are four ancillary problems that can be forseen to be associated with the above modifications.

The first ancillary problem is that there may be secondary adaptations in the translation apparatus that depend on the "bodies" of tRNAs being associated to specific codons, anticodons or amino acids. One example is a proposed proofreading of combinations of whole tRNAs and amino acids by EF-Tu (Dale, T. and Uhlenbeck, O. C. 2005). Another is associations of pairs of codons at the ribosomal A and P sites (Buchan, J. R. et al. 2006). The solutions to these problems are first to choose the types of tRNAs, and parts or those types, and codons to be exchanged carefully in such a way that minimizes these problems according to existing data, and second, when engineering a reproducing system such as a GMO, cell-line or virus, to use artificial selection to achieve compensatory adaptation of the encrypted translation system.

The second ancillary problem is that in certain organisms capable of a high rate of growth or for other reasons, there may be secondary adaptations of protein synthesis so that the number of codons for each amino acid and the number of genes for each tRNA and consequently their intracellular concentrations are related to the abundance in the proteome of the amino acids they are charged with, further that the gene dosage and intracellular concentrations of tRNAs are associated to the frequencies of codons in highly expressed genes. The solutions here are by following the design principles of minimal change, so that for example, intracellular concentrations of tRNAs for specific amino acids (and by implication, the regulation of the genes templating those tRNAs) are changed not at all or as little as possible, so that the relative covariation of tRNA concentrations and frequencies of codons cognate to those tRNAs is preserved as much as possible.

The third ancillary problem is that protein-coding genes may have codon-dependent regulatory structures and functionality that would be disrupted by the modified genetic code of the encrypted translational system. Three examples are regulatory attenuator leader peptides of biosynthetic operons in bacteria, that contain codons that might be affected by the genetic code change, functional secondary structures or absence of secondary structures in mRNAs, and codon-dependent alterations in the processivity of translation that are codon-dependent. Again, these problems may be met by careful design of the genetic code (in an organism-dependent way) and secondary compensatory evolution by artificial selection of the encrypted GMO. Design of the genetic code could possibly take into account modelling of mRNA secondary structures so that they would be preserved after the modification.

The fourth ancillary problem is that different groups of synonymous codons are decoded by (or "cognate to") sets of tRNAs (isoacceptors) that might have different kinds of anticodon stem-loop post-transcriptional modifications and therefore different codon reading degeneracies, that those post-transcriptional modifications might have determinants for their biosynthesis that lie outside the ASL, or have unknown determinants for their biosynthesis, and that there may be different numbers of these types of tRNAs decoding different sets of codons. Again, by the principle of least change, the solution by design is to exchange ASL templates from tRNA genes to other tRNA genes with the same wobble base if possible. In certain cases, because the decoding characteristics of different wobble position modified bases may depend on the bases at positions 34 and 35, we take into account the possible necessity of adding one or more tRNA genes to a synthetic genome in order to preserve the decoding complement of tRNAs for a set of related codons.

In light of these considerations, a nearly universal design strategy is to transplant, by in situ genetic alterations or synthetic design, alterations to the anticodon stem-loops (ASLs) of all tRNA paralogs templating Leu, Ser, and Ala tRNAs that decode some subset of the four-fold or two-fold degenerate codon family boxes for these three amino acids. These amino acids are relatively abundant and of sufficiently different biochemistry to achieve the aims of genetic encryption as described here.

Altering the anticodon-stem loop templates of tRNA genes in situ changes the decoding characteristics of the tRNA produced rather than its identity. Making these changes in the context of a transcription unit or genome preserves the regulatory context of the transcriptional unit and thereby the relationships between the amino acid-charging identities of tRNAs and their biosynthesis, which should thereby also preserve the concentrations of those tRNAs as defined by their amino acid-charging identities, from the perspective of the amino acid charging enzymes that charge them as well as the amino acid frequencies in the proteome. The regulation (and therefore concentrations) of the tRNAs is thereby defined by the amino acids they are charged with rather than the anticodons that they decode with! By also changing codons correspondingly with the anticodons, the covariation of tRNA anticodon concentrations and codon frequency ratios in the transcriptome are also preserved, which itself can also important to the performance and fitness of a living or synthetic translational system.

EXAMPLES

Illustrated below are some specific examples of the alterations of the genetic code of a biological reagent according to the present invention. These examples are provided as illustration only and should not be considered as limiting the scope of the invention, which is that of the appended claims.

Table 1 shows some examples of genetic code changes provided by this invention. In the table, the "N" in UCN, CUN, and GCN means A, C, G, or U, the "Y" in AGY means U or C, and the "R" in UUR means A or G. The row labeled "Standard Genetic Code" gives the assignments of amino acids to the codons designated in those columns and is specified as an example, as this invention is intended to cover the alteration of all known standard and variant genetic codes including the mycoplasma genetic code (Genetic Code #4 at http://www.ncbi.nlm.nih.gov/Taxonomy/Utils/wprintgc.cgi#SG4), mitochondrial genetic codes, and all naturally occurring or artificially otherwise altered genetic codes with which it is naturally compatible.

All of the altered genetic codes in this table involve the mutual reassignment of none, two-out-of-three, or all three of the four-fold degenerate codon boxes belonging to Serine, Leucine or Alanine—either alone or in combination with mutual reassignment of the two two-fold degenerate codon boxes for Serine and Leucine (called "SL2") in Table 1. In the following detailed design descriptions, we give examples of how to achieve the designs in Table 1 in a variety of organisms and solve the primary and ancillary problems described above.

TABLE 1

Overview of Example Genetic Code Changes Provided by this Invention

|  | GCN | CUN | UCN | UUR | AGY |
|---|---|---|---|---|---|
| Standard Genetic Code | Ala | Leu | Ser | Leu | Ser |
| SL2 | Ala | Leu | Ser | Ser | Leu |
| SL4 | Ala | Ser | Leu | Leu | Ser |
| SL6 | Ala | Ser | Leu | Ser | Leu |
| SA4 | Ser | Leu | Ala | Leu | Ser |
| SA4-SL2 | Ser | Leu | Ala | Ser | Leu |
| LA4 | Leu | Ala | Ser | Leu | Ser |
| LA4-SL2 | Leu | Ala | Ser | Ser | Leu |
| SLA4 | Ser | Ala | Leu | Leu | Ser |
| SLA4-SL | Ser | Ala | Leu | Ser | Leu |
| LSA4 | Leu | Ser | Ala | Leu | Ser |
| LSA4-SL2 | Leu | Ser | Ala | Ser | Leu |

Design 1: Partial Serine-Leucine Encryption (SL4) in a Larger Bacterial Genome.

Here by example of a larger free-living bacterium we use the example of *E. coli* K12. This is organism has a "mode 1" bacterial "tRNome" using a larger more redundant complement of about 46 types of tRNAs to decode all 61 sense codons (Marck, C. and Grosjean, H. 2002).

There are three major steps proposed in this design.

1. Swap the anticodon stem-loop templates (ASLs for short) of the tRNAs that decode the four-fold degenerate codons of Serine (the CUN codons) with the tRNAs that decode the four-fold degenerate codons of Leucine (the UCN codons), up to and including the 27-43 base-pair (see FIG. 1). In the case of *E. coli*, there are six such types of tRNAs, three types for Serine (called here Ser1, Ser2, and Ser5) and three types for Leucine (called here Leu1, Leu2, and Leu3). In *E. coli*, there exists a unique one-to-one correspondence between these types of tRNAs, such that each member of a pair of Serine and Leucine tRNAs has the same, possibly modified, base in the so-called wobble position, or base 34, and are therefore very likely to have the same decoding degeneracy (Nasvall, S. J. et al. 2004). ASLs are swapped between the pairs of types of tRNAs according to this correspondence of same decoding degeneracy. In the case of *E. coli*, this implies that ASLs are swapped between Ser1 and Leu3 (with anticodons cmo$^5$UAG and cmo$^5$UGA respectively, where cmo$^5$U stands for uridine-5-oxyacetic acid), Ser2 and Leu1 (with anticodons CAG and CGA respectively), and Ser5 and Leu2 (with anticodons GAG and GGA respectively). In practice, each type of tRNA is templated by multiple genes. Therefore, to be precise, the part of each tRNA gene templating the ASL is modified to make its sequence identical to that of the ASL template in a gene for the other type of tRNA in the correspondence defined above.

In general, the number of genes for each type of tRNA in a pair may differ and there may be sequence differences among the ASL templates of the genes to be copied from. For example, in *E. coli* K-12, the major leucine isoacceptor, Leu1, with a CAG anticodon, exists in four paralogs, three identical copies linked in the leuV operon, and one additional paralog in the argX operon. This latter fourth paralog differs by one base in the variable arm from the other paralogs. All of the other serine and leucine tRNA types exist in only one sequence form. Because the Leu1 sequence variation is not in the ASL, there is no ambiguity in how to execute this design.

However, if there are differences among ASLs of different paralogs of isoacceptors—serine and leucine in this case—I suggest to randomly sample by replacement the ASL templates of the isoacceptor paralogs to be copied from.

2. The change described in step 1 induces an alteration in the genetic code, and particularly in this case the decoding pattern of the four-fold degnerate Serine and Leucine tRNAs, but not the copy numbers or the operon or genomic contexts of those gene copies. As a result, the intracellular concentrations of tRNAs are expected to be the same after these ASL changes. To preserve encoded protein sequences, and much of the pre-existing translational performance of the mRNAs encoding those protein sequences, it is important to recreate by design the codon usage pattern of those four-fold degenerate codon family boxes as they were before the change. The way to do this is simply to reverse the order of "U" and "C" in all UCN and CUN codons in every protein-coding gene. That is, every UCA codon is altered to a CUA codon, while every CUA codon is altered to a UCA codon, and so on. The better characterized genetically the organism to be altered is, the more thoroughly annotated its protein-coding genes, and the better the chances are of encrypting all essential or otherwise requisite genes for a desired application. For application of the designs of this invention in *E. coli*, I would use the protein-coding gene models of EcoCyC (Keseler, I. M. et al. 2005; Karp, P. D. et al. 2007) to map all UCN and CUN codons to alter.

3. It is important to alter tRNA-dependent regulatory sequences so that they are also, to first degree, preserved after steps 1 and 2. Prime examples in *E. coli* are the protein-codon leader peptide coding genes of biosynthetic operons such as ilvL of the ilvLGMEDA biosynthetic operon, which contains CUN Leucine codons (Lawther, R. P. and Hatfield, G. W. 1980). These must also be altered to switch CUN and UCN codons so they can be read by the altered Leucine and Serine tRNAs in the encrypted genetic organism. Fortunately, these regulatory protein-coding open reading frames are annotated as genes in the aforementioned set of gene models from EcoCyC, and so their alteration was already covered in this specific case by step 2.

Figure 2:
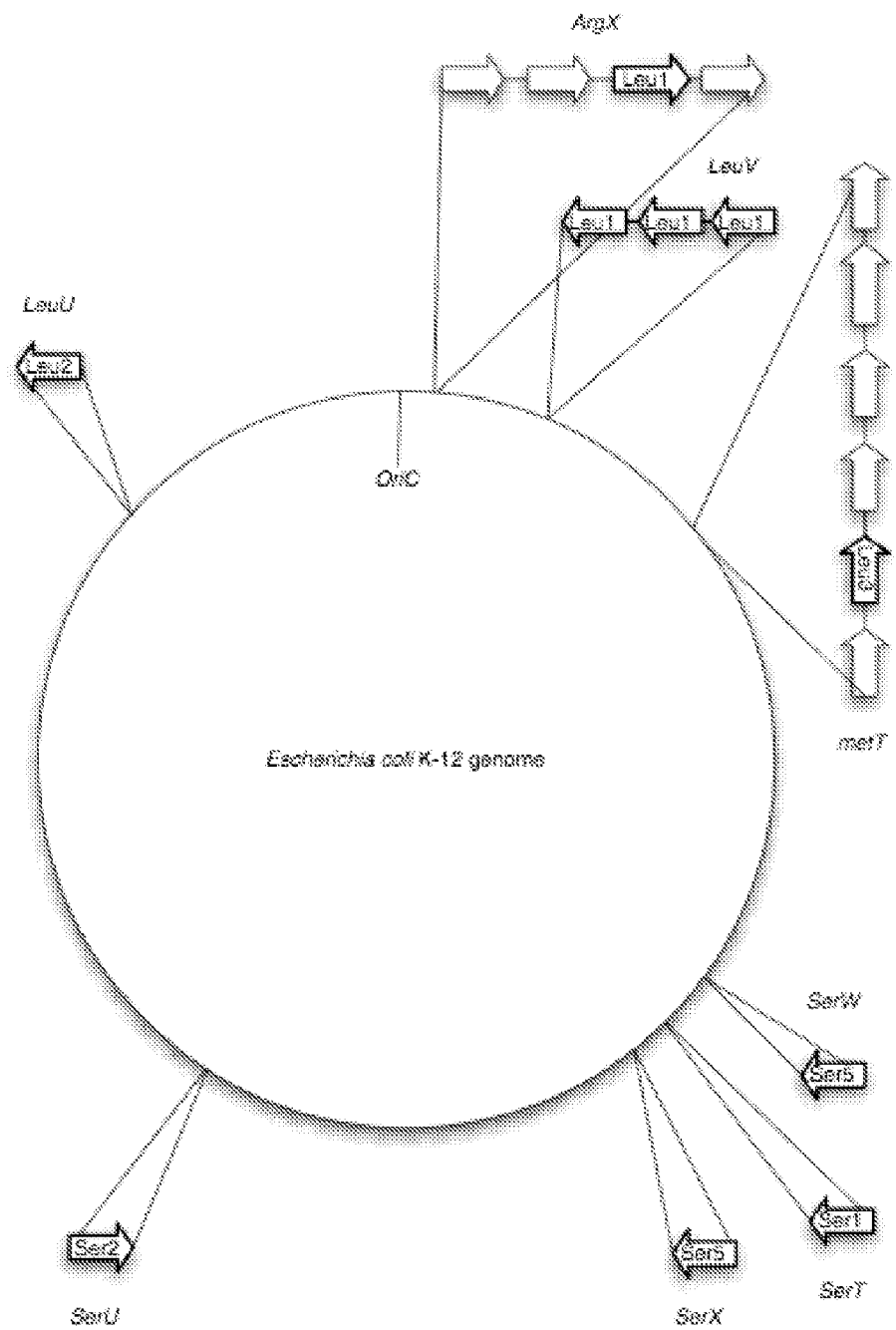
FIG. 2. Example of tRNA genes in *E. coli* K-12 showing which tRNA genes in which operons would be altered as described in the text to partly achieve SL4 encryption of this organism. Arrows indicate gene and operon strandedness. Operons are labeled in italic, and *E. coli* isoacceptor types are in roman. Arrows in bold are the only tRNA genes to be altered in SL4. The actual sequence changes are shown in FIG. 3.
Figure 3:
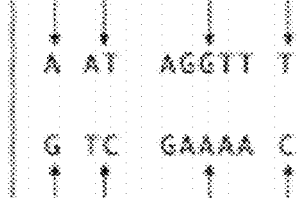
FIG. 3. All sequence changes to all tRNA paralogs required in *E. coli* K-12 to partly achieve SL4 encryption of this organism. All sequences are shown in 5' to 3' orientation starting from the first base (position 1 of the tRNA). The ASL templates from positions 27 to 43 are indicated by the inset boxes. In the particular case illustrated here, all paralogs shown in FIG. 2 are identical in sequence over the regions indicated, making the indicated sequence changes a sufficient and complete illustration of all changes necessary for SL4 encryption as described in the text. More generally, in the elementary changes of SL2, SL4, LA4, or SA4, tRNA paralogs of different types are paired and ASL template sequences (indicated by the inset boxes) are swapped across the pair in the manner indicated.

For diagrams illustrating how to alter a synthetic *E. coli* K-12 genome according to design 1 see FIGS. 2 and 3.

Design 2: Partial Serine-Leucine Encryption (SL4) in a More Minimal Bacterial Genome.

Here by example of a smaller free-living bacterium we use the example of *Mycoplasma*. This is organism has a "mode z" bacterial "tRNome" using a totally or nearly non-redundant complement of about 26 types of tRNAs to decode all 61 sense codons (Marck, C. and Grosjean, H.2002).

The organism *Mycoplasma capricolum* translates the Serine UCN and the Leucine CUN four-fold degenerate codon family boxes with two different single tRNAs each with an unmodified U in wobble position 34 (Andachi, Y. et al. 1989; Inagaki, Y. et al. 1995). In this design, like in Design 1, the ASL templates up to and including the bases that template the 27-43 base-pair are exchanged for all gene copies of tRNA-Ser-UGA and tRNA-Leu-UAG. Codons in protein-coding genes and known regulatory leader peptide coding regions are also exchanged as in Design 1.

Design 3: Total Serine-Leucine Encryption (SL6) in Bacterial Genomes, with a Description of the Genetic Code Change of SL2, and Strategies for Exchanging the Reading Capabilities of Isoacceptor Groups that are Different in Number While in Designs 1 and 2 we attempted to preserve as many features as possible, engineering exchanges of sequence information between analogous isoacceptors that decode the four-fold serine and leucine codon boxes. Designs 1 and 2 are conservative in that the risk of detrimental interactions that might influence codon translational reading efficiency, such as through base modification determinants that lie outside the ASL, are minimized, because the pattern of modifications and wobble bases are preserved. In this design, we prescribe change aiming for total and complete swapping of all leucine codons and serine codons. This design is an incremental development of Designs 1 and 2, including the changes described above. That is to say, in terms shown in Table 1, SL6 is carried out by implementing SL4 as described above, and in addition implementing SL2, which is described here.

In SL2, we make AGY codons encode leucine and UUR codons encode serine. Compared to SL4, effecting this change is more challenging, because both the number of tRNAs decoding these two sets of codons and their post-transcriptional modifications differ, reflecting that one set decodes purine-ending codons and the other pyrimidine-ending codons. The changes required may be more radical and possibly incur greater initial costs on organismal performance or fitness. SL6, however brings extra security of encrypting four additional codons, and complete encryption of all serine and leucine codons. In some organisms like E. coli, the AGY and UUR codons may include preferred codons for leucine and serine, making the extra security of encrypting them quite significant.

Bacterial tRNAs decoding these two two-codon family boxes have entirely different wobble position bases and modification patterns. In both E. coli and the mycoplasmas (de Crecy-Lagard, V. et al. 2007), only one serine tRNA isoacceptor translates the AGY serine codons with a GCU anticodon, while two different leucine isoacceptors translate the UUR codons, one with a cmnm$^5$UmAA anticodon and the other with a CmAA anticodon, where cmnm$^5$Um stands for 5-carboxymethylaminomethyl-2'-O-methyluridine and Cm stands for 2'-O-methylcytidine (Horie, N. et al. 1999).

Figure 4:
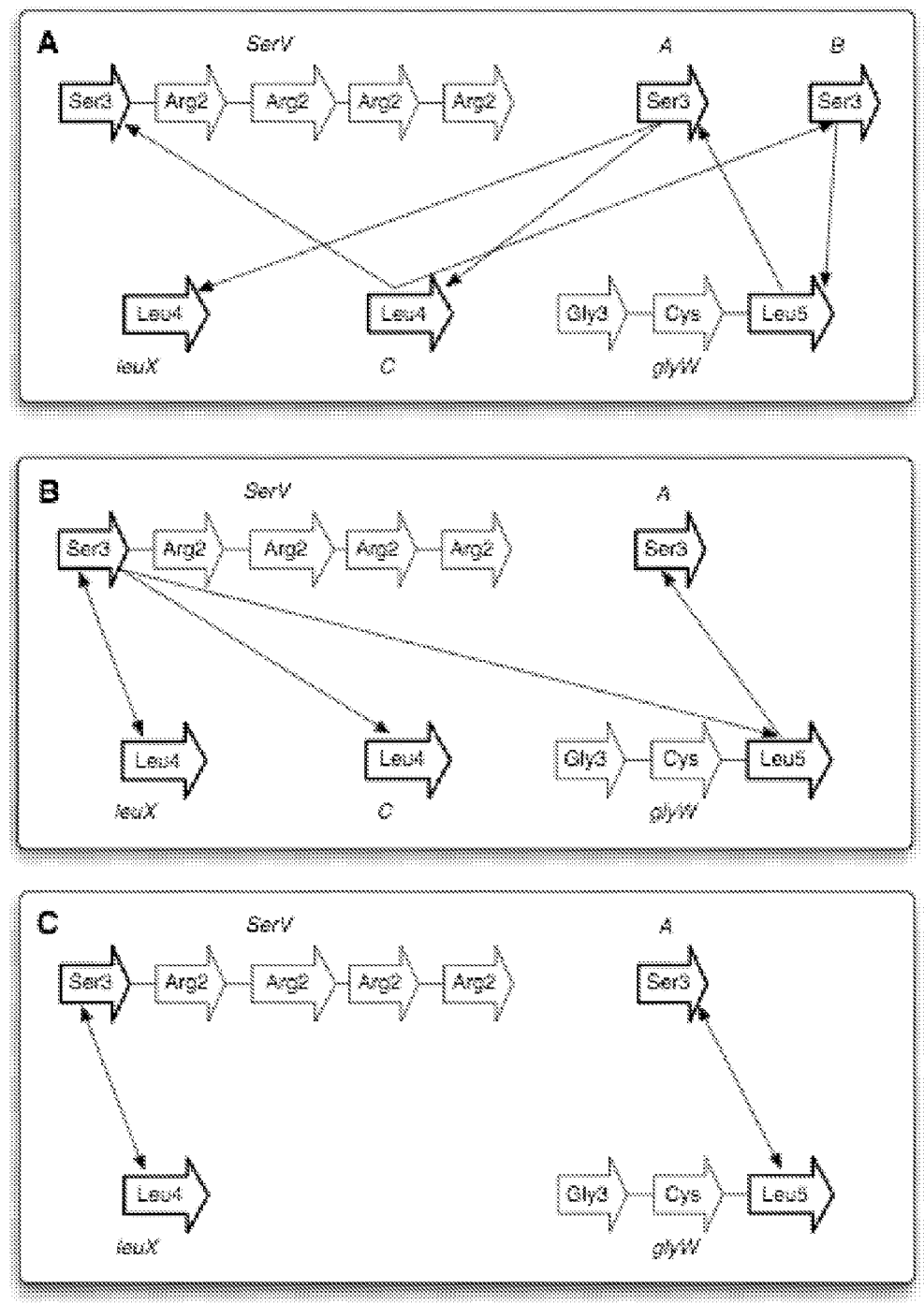
FIG. 4. Three valid examples of the random sampling strategy for rewriting ASL templates of isoacceptor groups decoding codon boxes that require different numbers of isoacceptor types (as defined by the wobble position 34), when the smaller group naturally has at least as many paralogs as the larger group has types. This is potentially important for any of the examples and specifically discussed in text in the context of SL2 in *E. coli* K-12, which concerns alteration of the operons serV, leuX and glyW. For the purposes of illustration, hypothetical operons A, B and C have been added. Fat arrows are tRNA genes, which are in operons if connected by lines and labeled by isoacceptor type. Skinny arrows indicate the direction in which the ASL template of one gene is used to rewrite that of another as in FIG. 3. Notice that in each example, every gene is rewritten but not every gene is the source of a rewrite, and that at least one copy of both Leu4 and Leu5 is always used as the source of a rewrite. The same rules may be used to handle the case of paralogs of the same types of isoacceptors with ASL template sequence differences.

To carry out SL2, the ASL templates of all genes for the single tRNA-Ser-GCU isoacceptor are randomly sampled (with replacement) and used to rewrite the ASL templates for all leucine tRNAs cognate to the UUR codons (with unmodified anticodons CAA and UAA). To make the AGY-reading Serine tRNAs read UUR codons, ASL templates up to and including the bases that template the 27-43 base-pair are randomly sampled from all tRNA-Leu-UAA and tRNA-Leu-CAA paralogs and used to rewrite the ASL templates of the tRNA-Ser-GCU genes, with the constraint that at least one of each kind of ASL is used as a template. This is called the random sampling strategy as shown in FIG. 4.

If there is only one tRNA-Ser-GCU gene to rewrite, then at least one duplicate Ser-tRNA-GCU gene must be engineered, and the two different UAA and CAA containing ASL templates should each overwrite the ASL template of at least one of those duplicates. The engineered gene copies could occur in the same operon or different operons as described below.

Because multiple tRNA gene operons occur in all bacterial genomes, even the smallest (such as mycoplasmas), we assume that the machinery for processing them occurs universally. Furthermore, tandemly repeated tRNAs are prone to repeat expansion and loss due to heterologous recombination (ref Andersson). This fact can be exploited in two ways: if the codons that the tRNAs templated by the tRNA-Ser-UAA and tRNA-Ser-CAA genes will translate are not preferred and in low frequency, it may be enough to ensure that at least one copy of each type of tRNA, tRNA-Ser-UAA and tRNA-Ser-CAA in the case of SL2, is retained and will not be overwritten by gene conversion or lost. Then the extra Serine gene can be designed with an alloaccepting tRNA gene copy in between. This is the interspersed genes in common operon strategy as shown by example for the E. coli serV operon in FIG. 5.

If on the other hand, codons these introduced tRNAs to be translated are very frequently and you wish to make it possible for an eGMO or other evolvable biological reagent to adapt in its tRNA gene dosage, it is desirable to have at least two copies of each paralog in tandem. This is the interspersed tandem duplicates in common operon strategy as shown by example for the E. coli serV operon in FIG. 5.

Figure 5:
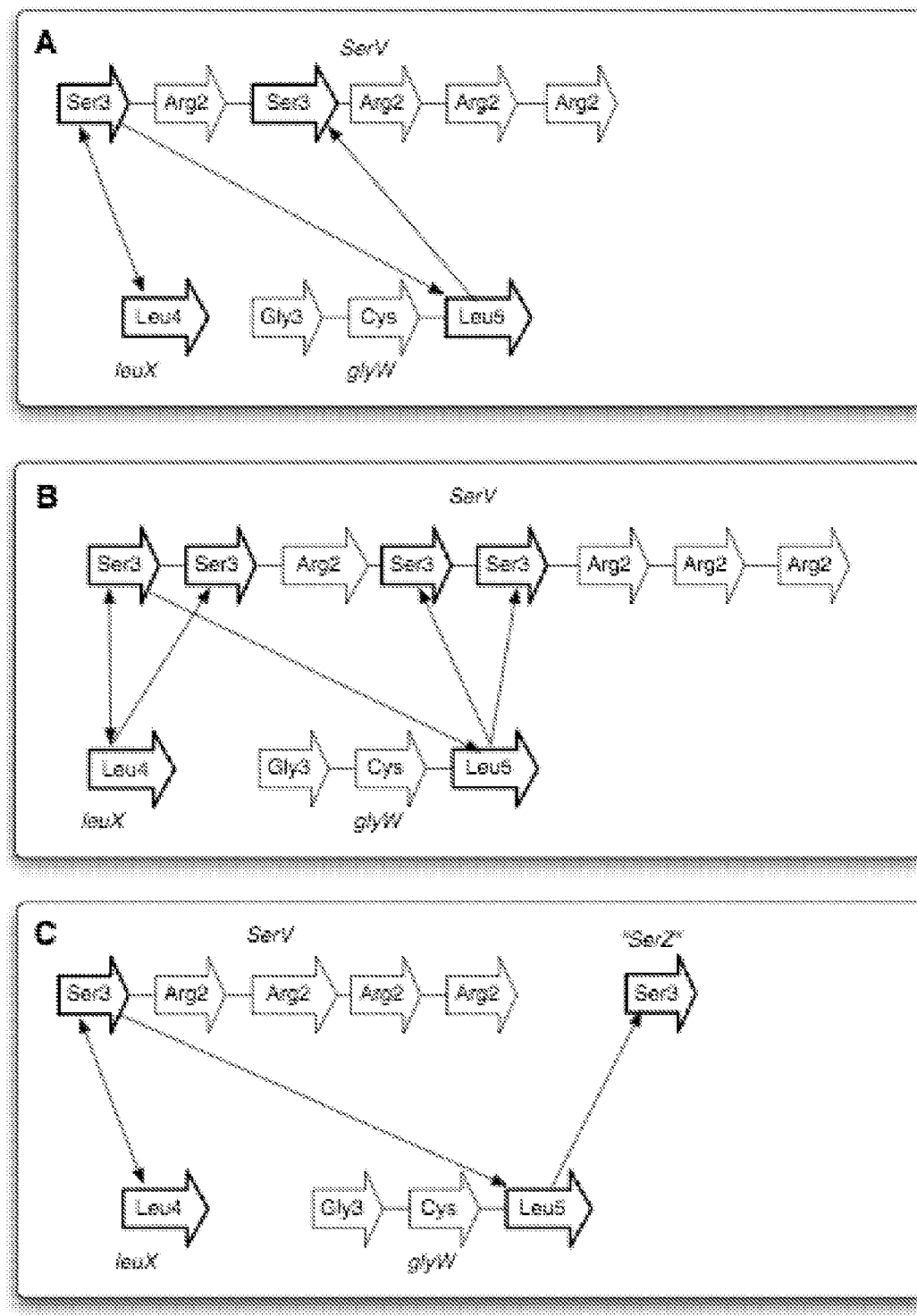
FIG. 5. Other strategies for rewriting ASL templates of isoacceptor groups decoding codon boxes that require different numbers of isoaccaptor types (as defined by the wobble position 34), when the smaller group does not have at least as many paralogs as the larger group has types. This is illustrated for the example of implementing SL2 in *E. coli* K12 as discussed in the text. A) The interspersed genes in common operon strategy, which requires artificial duplication of an existing gene within an operon, here the Ser3 gene in SerV. B) The interspersed tandem duplicates in common operon strategy and C) The operon duplication strategy which requires creation of an artificial operon with suitable regulatory elements placed so as to not disrupt other genes or their regulation. In all cases, the lone natural Ser3 gene in *E. coli* K12 SerV is used to create artificial paralogs.

If there is only one AGY-reading Serine tRNA gene copy in a genome to be engineered which appears in a single tRNA-gene operon, then it is advisable to duplicate the entire operon and insert it more than 6 Kb away in the genome. This is called the operon duplication strategy as shown in FIG. 5.

The principle we use to exchange the AGY and UUR codons in this design is to exchange preferred codons for each other. The frequencies of the two AGY Serine codons, AGC and AGU, and the two Leucine codons, UUA and UUG, are tabulated in all ribosomal protein genes of the genome to be engineered (if they exist) otherwise any other highly expressed genes of the translational system. The AGY codon of higher frequency in this tabulation is exchanged for the UUR codon of higher frequency in the tabulation in all protein-coding genes in the translation system, and similarly for the lower frequency AGY and UUR codons.

As described earlier, codons appearing in regulatory leader peptide regions (attenuators) must also be converted.

Design 4: Partial Alanine-Serine Encryption (SA4) or Alanine-Leucine Encryption (LA4) in Bacterial Genomes, with Additional Discussion of Handling Exchanges Between Isoacceptor Groups that are Different in Number One of the problems we deal with this in section may also arise in the partial serine-leucine encryption (SL4). It is related but not as difficult as that dealt with specifically in the change of the last section, namely SL2. That problem is how to deal with the case of when there are different numbers of types of isoacceptors genes for two fourfold degenerate family boxes that are to swap ASL templates. For example, in E. coli, that are three Serine isoacceptors that decode the UCN codons, previously described in design 1: Ser1, Ser2, and Ser5. However the Alanine codons are only decoded by two isoacceptors—Ala1 with a cmo$^5$UGC anticodon and Ala2 with a GGC anticodon (Nasvall, S. J. et al. 2007). It may very well be that Ala is different from Ser in not requiring an extra tRNA with C34 to decode codons that end in G (Nasvall, S. J. et al. 2004) (Kothe, U. and Rodnina, M. V. 2007). The question is how to exchange these tRNAs.

In such a case, we have a smaller isoacceptor group (in this case, GCN-reading Alanine tRNAs) and a larger group (in this case UCN-reading Serine tRNAs). In such a case, unlike SL2, some subset of the larger isoacceptor group will have the property that each member will have a unique correspondence to a member of the smaller group given by the unmodified base at wobble position 34. In the example, this correspondence is Ser1 and Ala1 (with U34 at the wobble base when unmodified) and Ser5 and Ala2 (with G34). The ASL templates of each pair of paralogous sets of isoacceptors can be exchanged, at least in part, like in designs 1 and 2. The isoacceptors of the larger group that are left unassigned by this correspondence because there is no isoacceptor in the smaller group sharing the same unmodified wobble base (e.g. Ser2 with C34 wobble base) can be secondarily paired off to one or more of the isoacceptors in the smaller group by the fact they can decode the same third codon base. In this case, Ser2 is paired to Ala1 because these both can decode G-ending codons.

It is easy to convert the larger isoacceptor group to read the codons read by the smaller isoacceptor group. The ASL templates up to the 27-34 base-pair of all genes for the smaller isoacceptor group are randomly sampled (with replacement) and to rewrite the ASL templates for all isoacceptor genes of the larger isoacceptor group according to the correspondence described in the previous paragraph.

To convert the smaller isoacceptor group to read the codons read by the larger isoacceptor group one of the strategies described above for SL2 must be employed (random sampling, operon duplication, interspersed duplicate genes, interspersed tandem duplicate genes). More specifically, in the case of SA4 in *E. coli*, because there are multiple paralogs for the Ala1 gene, I would follow the random sampling strategy and randomly sample among ASL templates of Ser1 and Ser2 genes to copy over ASL templates of all Ala1 genes, ensuring that there is at least one Ser2 ASL included after sampling. I might additionally impose the constraint that there is at most one Ser2 ASL among the rewritten Ala1 isoacceptor paralogs.

To complete SA4 or LA4 encryption, all GCN codons in all protein-coding genes or regulatory regions should be rewritten into UCN codons and vice versa (for SA4) or all GCN codons should be rewritten to CUN codons and vice versa (for LA4), in all cases retaining the same third position base.

SA4 and LA4 may be combined simultaneously with SL2 as previously described to achieve more extensive encryption.

In some organisms, at least *E. coli* K-12 and probably other organisms, a special role of alanine codons near the initiation region (specifically the second codon) correlated with high expression has been reported. This may depend on the presence of alanine as the second N-terminal residue on translation and processing, which like other early N-terminal residues modulates protein stability and N-terminal formyl-methionine or methionine processing, and interaction of the nascent peptide chain with the ribosomal tunnel. In this case, serine is often a second preferred amino acid (Tats, A. et al. 2006). However, the GCN codons themselves may provide important biological roles in the interactions of mRNAs with the ribosome (as reviewed in (Tats, A. et al. 2006)). The proceeding considerations suggest a potential alteration which may give an advantage when employed with SA4 and SA4-SL2 over any other encryption involving alanine, including LSA4, SLA4 (described below), LA4, LA4-SL2, and over SA4 and SA4-SL2 when not incorporating this alteration. That alteration is namely to leave GCN codons unconverted when they occur at the second codon position, especially in highly expressed genes. These will now encode Serine, which as previously mentioned is apparently preferable second alternative amino acid for the peptide-dependent effects and retains the GCN signal for the mRNA dependent effects.

Design 5: Partial Alanine-Serine-Leucine Encryption in Prokaryotic Genomes (LSA4 or SLA4).

Technically, all elements necessary to rotate alanine, leucine, and serine over the GCN, CUN, and UCN codon family boxes have already been described above as elements of SL4, LA4 and SA4. Instead of reciprocally overwriting the ASL templates of all paralogs between only two of the three isoacceptor groups, ASL templates are used to overwrite all paralogs of all three isoacceptor groups in a rotation of cycle-length three. For instance, suppose if all paralogous alanine tRNAs are converted to read UCN codons by overwriting their ASL templates with randomly sampled ASL templates from paralogous UCN-reading serine tRNAs (as previously described for SA4), all paralogous UCN-reading serine tRNAs are converted to read CUN codons by overwriting their ASL templates with randomly sampled ASL templates from paralogous CUN-reading leucine tRNAs (as previously described for SL4), and all paralogous CUN-reading leucine tRNAs are converted to read GCN codons by overwriting their ASL templates with randomly sampled ASL templates from alanine tRNAs (as previously described for LA4). This partly achieves LSA4 encryption ("LSA4" here stands for reassignment of codons from their usual meaning in the standard genetic code as given in column order of Table 1, which is "SLA." It is not to be confused with Anticodon Stem-Loop). Also, in LSA4 encryption, all GCN codons in all protein-coding genes or codon-dependent regulatory structures must be altered to UCN codons as described previously for SA4, all UCN codons in all protein-coding genes or codon-dependent regulatory structures must be altered to CUN codons as described previously for SL4, and all CUN codons in all protein-coding genes or codon-dependent regulatory structures must be altered to GCN codons as described previously for LA4.

Alternatively, suppose if all paralogous alanine tRNAs are converted to read CUN codons by overwriting their ASL templates with randomly sampled ASL templates from paralogous CUN-reading leucine tRNAs (as previously described for LA4), all paralogous CUN-reading leucine tRNAs are converted to read UCN codons by overwriting their ASL templates with randomly sampled ASL templates from paralogous UCN-reading serine tRNAs (as previously described for SL4), and all paralogous UCN-reading serine tRNAs are converted to read GCN codons by overwriting their ASL templates with randomly sampled ASL templates from alanine tRNAs (as previously described for SA4), this partly achieves SLA4 encryption. Also, in SLA4 encryption, all GCN codons in all protein-coding genes or codon-dependent regulatory structures must be altered to CUN codons as described previously for LA4, all CUN codons in all protein-coding genes or codon-dependent regulatory structures must be altered to UCN codons as described previously for SL4, and all UCN codons in all protein-coding genes or codon-dependent regulatory structures must be altered to GCN codons as described previously for LA4.

To complete LSA4 or SLA4 encryption, the potential problems from different numbers of isoacceptors decoding the different four-fold codon family boxes in a given biological reagent or translation system may be overcome by following the strategies previously described (random sampling, operon duplication, interspersed duplicate genes, interspersed tandem duplicate genes).

LSA4 and SLA4 may be combined simultaneously with SL2 as previously described to achieve more extensive encryption.

Design 6: Genetic Encryption in Eukaryotes.

Application of the designs described above to eukaryotes requires the extra consideration that nuclear-originating tRNAs may be imported into mitochondria. If two or more of the types of tRNAs discussed in the examples above (serine, alanine and leucine) are not imported into either mitochondria or chloroplasts, and if the assumptions of the designs apply to the eukaryotic organism, cell line, eukaryotic derived in vitro translation system or other eukaryotic derived biological reagent, then the designs described above may be directly applied to the nuclear genome or genes in questions as described above. Import of a tRNA into an organeller compartment may require additional encryption of the protein-coding genes in the genome of that organelle to be compatible with the alterations, as well as verification that, if there is a distinct organeller aminoacyl tRNA-synthetase interacting with the tRNA in that compartment, that that synthetase also follows the assumptions inherent in the design according to the invention, namely ASL and especially anticodon independence.

In the bean *Phaseolus*, nuclear-produced Leu-tRNA (with unmodified CAA anticodon) is imported into mitochondria (Small, I. et al. 1992). Closely related species can differ in whether cytosolic Serine or other tRNAs are imported into mitochondria (Kumar, R. et al. 1996). Nuclear-produced Ala-tRNA and other Leu tRNAs are imported into mitochondria in potato (Dietrich, A. et al. 1992), *Arabidopsis* (Dietrich, A. et al. 1996) and other plants. However, four-base insertions into the anticodon stem-loop of Leucine tRNA (Small, I. et al. 1992) and Alanine tRNA (Dietrich, A. et al. 1996) do not prevent those tRNAs from being imported into mictochondria. This suggests that the designs of this patent, at least LA4, could successfully be used to create encrypted genetically modified plants, so long as both nuclear and mitochondrial protein-coding genes could be altered accordingly.

Design 7: Alteration of Designs 1-6 in Organisms for which Partial Aminoacylation Dependence on ASL Elements Outside the Anticodon have been Demonstrated.

In an organism in which one or both of native SerRS or LeuRS has been shown to recognize an ASL element outside the anticodon, the demonstrated structural features can be selectively retained (unaltered) when making the sequence changes to ASL templates in tRNA genes prescribed in designs 1 through 4.

As an example, a G30:C40 base-pair was found to be important for binding of tRNAs to SerRS in the archaeon *Methanosarcina barkeri*, and this feature appears to be conserved among serine tRNAs in archaea (Korencic, D. et al. 2004). A serine tRNA being altered to read leucine codons in an encrypted translational system or organism with archaeal SerRS might swap in leucine ASL features while retaining this base-pair. In this particular example given here, at least one leucine ASLs in M. barkeri happens to share the G30:C40 base-pair with serine tRNA ASLs, obviating the additional consideration of this design when this leucine ASL is used as a basis for serine ASL modification.

All designs above should be construed as suggestions—subsets of and additions to ASLs may be used as a basis of codon reading transfer (retaining aminoacylation identity) to tRNAs adjusting in response to experimental data. In particular, aminoacylation determinants within the ASL can be retained, and codon reading and base modification determinants (that influence codon reading) can be altered outside the ASL.

Implementation of the Examples

1. Implementation of the Prescribed Genetic Changes

Implementation of the designs of this invention requires the ability to engineer a genome or set of genes with a potentially very large number of unnatural (that is, not naturally occurring) prescribed sequence characteristics. For an in vitro translation system, this can be accomplished by artificial gene synthesis. For an example of an enabling technology, see Lathrop et al. (U.S. Pat. No. 7,262,031 B2).

A useful method for creating an encrypted GMO, virus or cell-line incorporating the prescribed designs is to synthesize an entire genome incorporating the changes here prescribed, and in the case of a bacterium or eukaryotic cell-line, transfer it into a recipient cell by genome transplantation. To date, synthetic genomes resulting in de novo synthesis of viable virus has been reported for poliovirus (Cello, J. et al. 2002) and a bacteriophage with a larger genome (Smith, H. O. et al. 2003). Technologies continue to develop expanding the size of genomes accessible to synthesis (Tian, J. et al. 2004). The company Synthetic Genomics Inc. has publically declared its intention to engineer bacteria and plants with synthetic genomes (http://www.syntheticgenomics.com) and received significant private investment. Scientists in this company recently achieved genome transplantation among bacteria (Lartigue, C. et al. 2007), which is essential for creating GMOs with synthetic genomes. Scientists and ethicists treat synthetic genomics as an inevitability (see e.g. Cho, M. K. et al. 1999 and references therein).

There is a long record of using selection to achieve impressive adaptive alterations in the genetic code (Wiltschi, B. and Budisa, N. 2007). Here, by simultaneously altering all protein-coding genes in concordance with a limited and specific alteration of the reading specificities of certain tRNAs, it is very likely that selection will be effective in ameliorating secondary deleterious traits created by the alteration.

2. The Prescribed Alterations to tRNAS Will Result in Efficient Swapping of Amino Acid Charging in vitro and in vivo and Thereby Alteration of the Genetic Code Here we collect evidence that the proposed alterations of tRNA ASLs would not interfere with the serylation, leucylation, or alanylation specificities of the tRNAs so altered. As a result, by altering the ASLs of those tRNAs so that they have different anticodons, the reading specificities of those tRNAs would be altered without also altering their amino acid charging specificities. As a result, the genetic code of the GMO or in vitro translation system would be altered.

The evidence reviewed here pertains to the interactions of tRNAs with aminoacyl-tRNA synthetases in three systems: the serine, leucine, and alanine systems, because it is these systems that the designs given by example here pertain to.

Serine is the only amino acid encoded in the standard genetic code with codons that differ in every codon position (UCN codons and AGY codons, where N is any base and Y pyrimidine). This fact alone suggests strongly that the anticodon is not a recognition element for seryl-tRNA synthetase (SerRS) in any organism. In vitro serylation studies have shown broad and general evidence supporting this conclusion. For instance, a tyrosine tRNA from the bacterium *E. coli* could be altered to become a serine tRNA without any changes to its anticodon stem-loop (ASL) (Himeno, H. et al. 1990). This implies that a tyrosine ASL could be transplanted into an *E. coli* serine tRNA without altering its fitness for serylation. Experimentally, an in vitro study of serylation recognition elements, that included an experimental assay for serylation activity of an in vitro transcribed leucine tRNA required no bases in the anticodon stem, and conversion of the 27-43 base-pair had no effect (Asahara, H. et al. 1994).

The anticodon stem-loop-independence of serine tRNA recognition in vitro serylation assays has been demonstrated in every organism so-far assayed, including yeast (Himeno, H. et al. 1997) and human (Achsel, T. and Gross, H. J. 1993). A human valine tRNA could be transformed into a serine tRNA even after retaining a valine anticodon stem-loop (ASL), using whole cell extracts from HeLa cells (Achsel, T. and Gross, H.J. 1993). Another in vitro study showed that a leucine tRNA could be completely converted to an efficient serine acceptor, abolishing leucine acceptance, by changing a single nucleotide far away from the anticodon arm (Breitschopf, K. and Gross, H. J. 1994). A similar alteration far from the anticodon arm was sufficient to make a leucine to serine identity conversion in yeast (Himeno, H. et al. 1997). The entire anticodon stem-loop ASL of a human serine tRNA could be deleted while still retaining nearly perfect substrate activity for human SerRS (Heckl, M. et al. 1998).

Only the second base of the anticodon is common among the five isoacceptors of tRNA Leu in *E. coli*. Substitution of this base in an *E. coli* leucine tRNA proved that the anticodon of tRNA Leu is not recognized by LeuRS in this species (Shimizu, M. et al. 1992). Experimental in vitro acceptor specificity conversions from both E. coli tRNA Ser and tRNA Tyr to leucine acceptance do not require any changes in the ASL, consistent with the implied leucylation functionality of a leucine tRNA designed with a serine ASL (Asahara, H. et al. 1993). Further in vitro studies with E. coli AlaRS show that the ASL and variable arm can be completely deleted from a leucine tRNA and it can still function as an efficient substrate for LeuRS (Larkin, D. C. et al. 2002).

In humans, no change in the anticodon stem-loop (ASL) domain is required in order to convert a human serine tRNA and valine tRNA into an efficient leucine acceptor (Breitschopf, K. et al. 1995), implying that a Serine tRNA ASL can be transplanted onto a human leucine tRNA to change its reading characteristics without altering its leucine charging specificity. This observation likely holds for a variety of other eukaryotes except, at least, for baker's yeast (see below). For instance, in plants, it has been shown that a four-base insertion into the anticodon loop of a leucine tRNA did not alter leucylation efficiency with purified LeuRS from the cytoplasm of the bean Phaseolus vulgaris in vitro, when compared to wild-type leucine tRNA transcript (Small, I. et al. 1992). Those authors concluded that no part of the ASL is involved in recognition by bean leuRS even though the 3' half of the ASL is protected from chemical attack by bean leucyl-tRNA synthetases (Dietrich, A. et al. 1990).

In vitro, leucylation of tRNAs by leuRS from the Baker's yeast Saccharomyces cerevisiae has been shown to depend on ASL nucleotides, particularly A35 and G37 (Soma, A. et al. 1996). Yeasts are the only eukaryotes in which any of the three tRNA types discussed in our designs (Ser, Leu and Ala) have been shown to have anticodon stem-loop dependence. Ironically, this group includes the only eukaryotic organism with an altered nuclear genetic code involving a change in amino acid sense rather than assignment of sense to a stop codon, and this change is reassignment of CUG from Ser to Leu (see e.g. (Miranda, I. et al. 2006)). Nevertheless, SA4 encryption described herein should still be applicable to genetic encryption of systems derived from even this organism.

In archaea, quite notably, experimental transplantations of entire anticodon stem-loops were carried out in in vitro assays demonstrating that exchange of serine and leucine anticodon stem-loops (ASLs) between leucine and serine tRNAs (up to and including the 27-43 base-pair) caused only a 0.87-fold reduction in leucylation activity on a leucine tRNA and no gain in leucylation activity by a serine tRNA with LeuRS and tRNAs from the archaeon Haloferax volcanii (Soma, A. et al. 1999).

There is extensive evidence for universal ASL-independence of alanine tRNAs in a variety of prokaryotes and eukaryotes, for a review, see (Giege, R. et al. 1998). The ASL-independence of Alanyl-tRNA synthetases is exemplified by their ability to charge a variety of RNAs lacking an ASL entirely such as microhelices (Francklyn, C. and Schimmel, P. 1989) or tmRNAs and viral tRNA-like mimics, as reviewed in (Giege, R. et al. 1998).

The previously summarized in vitro evidence for anticodon stem-loop independence of aminoacylation of serine, leucine and alanine tRNAs is abundantly well-complemented by in vivo evidence. In E. coli, nonsense suppressors retain aminoacylation identity despite alteration of the anticodon for serine, leucine (Normanly, J. et al. 1986), and alanine (Normanly, J. et al. 1990) tRNAs. Furthermore, a leucine nonsense suppressor can be converted to a serine nonsense suppressor by changing only eight base-pairs, all outside the ASL (Normanly, J. et al. 1992). The opposite identity change of suppressors to leucine identity from serine identity can also be affected without changes to the anticodon stem-loop (Tocchini-Valentini, G. et al. 2000).

Eukaryotic nonsense supressors derived from have also been studied in abundance. The previously mentioned in vitro studies of human serylation recognition elements were based on a study showing functional suppression of human serine tRNA gene derivatives (Capone, J. P. et al. 1985). Leucylated nonsense suppressors also demonstrate anticodon independence of leucylation in leucine tRNAs from the tobacco plant (Carneiro, V. T. et al. 1993). Betzner et al. created an artificial amber (UAG) suppressor tRNA_Leu gene (supL) in Arabidopsis that was able to suppress amber codons in vivo (Betzner, A. S. et al. 1997). Murakami et al. isolated a naturally occurring Ser CGA Amber suppressor from a forward genetic screen, in the nuclear genome of Chlamydomonas (Murakami, S. et al. 2005).

3. The Prescribed Alterations to tRNAS Will Preserve Codon Reading Characteristics and Efficiency.

The herein prescribed design calls for the exchange of entire anticodon-stem loops ASLs up to and including the 27-43 basepair. There are several reasons for this. The first is that other bases in the ASL are correlated with the anticodon triplet, a finding first reported as the "extended anticodon hypothesis," which postulates tuning interactions in the ASL for translational efficiency, specifically against the "cardinal nucleotide," base 36 of the anticodon, which is cognate to the first codon position (Yarus, M. 1982). The 27-43 base-pair has been implicated to affect codon-anticodon pairing (Schultz, D. W. and Yarus, M. 1994; Schultz, D. W. and Yarus, M. 1994). These hyptheses originally introduced on analysis of E. coli sequences, has since been extended and found general support when assessed in other prokaryotes and eukaryotes (ref BuchanEtA106, SaksConnery07).

Because the codon reassignments prescribed are implemented through alteration of the cardinal nucleotides of tRNAs, to preserve coadapted structures in the ASL that may contribute to translational efficiency and accuracy of these tRNAs at the ribosome, we prescribe exchanges of entire ASLs.

Another property of translational efficiency that is preserved in design 1 is the concentrations and regulation of tRNA isoacceptors, and the frequencies of codons they are cognate to. Because the ASL templates of tRNA genes are changed in situ in their natural genetic contexts, their regulation and presumably, concentrations will be unaltered by the prescribed changes. Because the ASLs of analogous tRNAs are exchanged, assuming that the ASL post-transcriptional base modifications are assumed to be determined locally within the ASL, the codon reading characteristics of the tRNAs within a four-fold degenerate family box will be unaltered by the prescribed changes. Because codons in protein-coding genes are then altered in parallel to the tRNA anticodons, the correlation of codon usage and tRNA concentrations is also preserved in the prescribed changes.

Some designs herein should be robust even if ASL modification determinants lie outside the ASL, such as the example given of applying SL4 in E. coli K-12. Other designs would perhaps work less well unless the ASL modification determinants themselves lay inside the ASL or could be also engineered if necessary as in design 7.

To the extent they have been studied, ASL modification determinants seem often to lie inside the ASL (Tsang, T. H. et al. 1983; Qian, Q. and Bjork, G. R. 1997; Redlak, M. et al. 1997; Jager, G. et al. 2004; Helm, M. 2006).

4. The Prescribed Alterations will Result in Genetic Isolation of the Encrypted GMO or in vitro Translation System: an Encrypted Gene in an Unencrypted Translational Context or an Unencrypted Gene in an Encrypted Context will Both have a High Probability of Producing Nonfunctional Protein.

General observations support strongly that the encryption described here will be effective in blocking the expression of functional protein information when an encrypted gene is moved into a nonencrypted or very differently encrypted background, or a nonencrypted gene is moved into an encrypted background. L-leucine is the most abundant building block of all proteins (occurrence leucine 9.1%, http://www.cmbi.kun.nl/gvteach/aainfo/). Serine often plays a role as catalytic residues in essential proteins (Brenner, S. 1988) and alanine is frequently used to scan for residue functionality by "ala-scanning" to knock them out. Leucine, serine and alanine differ in size and polarity.

In the plant *Arabidopsis*, it was shown that an alanine-tRNA with an anticodon mutation could still be alanylated resulting in auxin resistance and many other pleiotropic mutations such as developmental defects (Perry, J. et al. 2005).

The altered assignment of Serine to the standard leucine CUG codon in some species of *Candida* prevents the heterologous expression of functional cytochromes P450 52A4 and 52A5 proteins in other yeasts with a standard code, making them unstable and subject to proteolysis (Zimmer, T. and Schunck, W.H. 1995), entirely nonfunctional (Sugiyama, H. et al. 1995) or toxic to the cell (Leuker, C. E. and Ernst, J. F. 1994).

Mutant leucine tRNAs Leu (with altered ASLs) imported to mitochondria affected pollen production specifically. In plants, mitochondrial gene expression defects often cause male sterility (Small, I. et al. 1992).

5. The Trait of Encryption Itself is Very Unlikely to be Either Lost or Acquired by any Natural Means of Genetic Exchange.

The essence of the genetic restriction in genetic encryption is the sheer enormity in number of genetic changes required to carry it out. The mutual co-adaptation in the design between multiple tRNA genes, eradicating conflicting "polysemous" meanings of codons, and the entire complement of protein-coding genes in a genome means that partial acquisition of some of the tRNA or protein-coding genes from an encrypted background or alternatively encrypted background will have deleterious fitness effects as discussed above, and therefore will be unlikely to retained, making full acquisition of the encrypted trait by further acquisition of genes or adaptation very unlikely.

Bibliography

Achsel, T. and H. J. Gross. 1993. Identity determinants of human tRNA(Ser): sequence elements necessary for serylation and maturation of a tRNA with a long extra arm. *Embo J* 12(8): 3333-3338.

Andachi, Y., F. Yamao, A. Muto and S. Osawa. 1989. Codon recognition patterns as deduced from sequences of the complete set of transfer RNA species in *Mycoplasma capricolum*. Resemblance to mitochondria. *J Mol Biol* 209 (1): 37-54.

Asahara, H., H. Himeno, K. Tamura, N. Nameki, T. Hasegawa and M. Shimizu. 1993. Discrimination among *E. coli* tRNAs with a long variable arm. *Nucleic Acids Symp Ser* (29): 207-208.

Asahara, H., H. Himeno, K. Tamura, N. Nameki, T. Hasegawa and M. Shimizu. 1994. *Escherichia coli* seryl-tRNA synthetase recognizes tRNA(Ser) by its characteristic tertiary structure. *J Mol Biol* 236(3): 738-748.

Betzner, A. S., M. P. Oakes and E. Huttner. 1997. Transfer RNA-mediated suppression of amber stop codons in transgenic *Arabidopsis thaliana. Plant J* 11(3): 587-595.

Breitschopf, K., T. Achsel, K. Busch and H. J. Gross. 1995. Identity elements of human tRNA(Leu): structural requirements for converting human tRNA(Ser) into a leucine acceptor in vitro. *Nucleic Acids Res* 23(18): 3633-3637.

Breitschopf, K. and H. J. Gross. 1994. The exchange of the discriminator base A73 for G is alone sufficient to convert human tRNA(Leu) into a serine-acceptor in vitro. *Embo J* 13(13): 3166-3169.

Brenner, S. 1988. The molecular evolution of genes and proteins: a tale of two serines. *Nature* 334(6182): 528-530.

Buchan, J. R., L. S. Aucott and I. Stansfield. 2006. tRNA properties help shape codon pair preferences in open reading frames. *Nucleic Acids Res* 34(3): 1015-1027.

Capone, J. P., P. A. Sharp and U. L. RajBhandary. 1985. Amber, ochre and opal suppressor tRNA genes derived from a human serine tRNA gene. *Embo J*4(1): 213-221.

Carneiro, V. T., G. Pelletier and I. Small. 1993. Transfer RNA-mediated suppression of stop codons in protoplasts and transgenic plants. *Plant Mol Biol* 22(4): 681-690.

Cho, M. K., D. Magnus, A. L. Caplan and D. McGee. 1999. Policy forum: genetics. Ethical considerations in synthesizing a minimal genome. *Science* 286(5447): 2087, 2089-2090.

Dale, T. and O. C. Uhlenbeck. 2005. Amino acid specificity in translation. *Trends Biochem Sci* 30(12): 659-665.

de Crecy-Lagard, V., C. Marck, C. Brochier-Armanet and H. Grosjean. 2007. Comparative RNomics and modomics in mollicutes: prediction of gene function and evolutionary implications. *IUBMB Life* 59(10): 634-658.

Dietrich, A., L. Marechal-Drouard, V. Carneiro, A. Cosset and I. Small. 1996. A single base change prevents import of cytosolic tRNA(Ala) into mitochondria in transgenic plants. *Plant J* 10(5): 913-918.

Dietrich, A., P. Romby, L. Marechal-Drouard, P. Guillemaut and R. Giege. 1990. Solution conformation of several free tRNALeu species from bean, yeast and *Escherichia coli* and interaction of these tRNAs with bean cytoplasmic Leucyl-tRNA synthetase. A phosphate alkylation study with ethylnitrosourea. *Nucleic Acids Res* 18(9): 2589-2597.

Dietrich, A., J. H. Weil and L. Marechal-Drouard. 1992. Nuclear-encoded transfer RNAs in plant mitochondria. *Annu Rev Cell Biol* 8: 115-131.

Francklyn, C. and P. Schimmel. 1989. Aminoacylation of RNA minihelices with alanine. *Nature* 337(6206): 478-481.

Giege, R., M. Sissler and C. Florentz. 1998. Universal rules and idiosyncratic features in tRNA identity. *Nucleic Acids Res* 26(22): 5017-5035.

Heckl, M., K. Busch and H. J. Gross. 1998. Minimal tRNA (Ser) and tRNA(Sec) substrates for human seryl-tRNA synthetase: contribution of tRNA domains to serylation and tertiary structure. *FEES Lett* 427(3): 315-319.

Helm, M. 2006. Post-transcriptional nucleotide modification and alternative folding of RNA. *Nucleic Acids Res* 34(2): 721-733.

Hills, M. J., L. Hall, P. G. Arnison and A. G. Good. 2007. Genetic use restriction technologies (GURTs): strategies to impede transgene movement. *Trends Plant Sci* 12(4): 177-183.

Himeno, H., T. Hasegawa, T. Ueda, K. Watanabe and M. Shimizu. 1990. Conversion of aminoacylation specificity from tRNA(Tyr) to tRNA(Ser) in vitro. *Nucleic Acids Res* 18(23): 6815-6819.

Himeno, H., S. Yoshida, A. Soma and K. Nishikawa. 1997. Only one nucleotide insertion to the long variable arm confers an efficient serine acceptor activity upon *Saccharomyces cerevisiae* tRNA(Leu) in vitro. *J Mol Biol* 268(4): 704-711.

Horie, N., Z. Yamaizumi, Y. Kuchino, K. Takai, E. Goldman, T. Miyazawa, S, Nishimura and S. Yokoyama. 1999. Modified nucleosides in the first positions of the anticodons of tRNA(Leu)4 and tRNA(Leu)5 from *Escherichia coli*. *Biochemistry* 38(1): 207-217.

Inagaki, Y., A. Kojima, Y. Bessho, H. Hori, T. Ohama and S. Osawa. 1995. Translation of synonymous codons in family boxes by *Mycoplasma capricolum* tRNAs with unmodified uridine or adenosine at the first anticodon position. *J Mol Biol* 251(4): 486-492.

Jager, G., R. Leipuviene, M. G. Pollard, Q. Qian and G. R. Bjork. 2004. The conserved Cys-X1-X2-Cys motif present in the TtcA protein is required for the thiolation of cytidine in position 32 of tRNA from *Salmonella enterica* serovar Typhimurium. *J Bacteriol* 186(3): 750-757.

Karp, P. D., I. M. Keseler, A. Shearer, M. Latendresse, M. Krummenacker, S. M. Paley, I. Paulsen, J. Collado-Vides, S. Gama-Castro, M. Peralta-Gil, et al. 2007. Multidimensional annotation of the *Escherichia coli* K-12 genome. *Nucleic Acids Res*.

Keseler, I. M., J. Collado-Vides, S. Gama-Castro, J. Ingraham, S. Paley, I. T. Paulsen, M. Peralta-Gil and P. D. Karp. 2005. EcoCyc: a comprehensive database resource for *Escherichia coli*. *Nucleic Acids Res* 33(Database issue): D334-337.

Korencic, D., C. Polycarpo, I. Weygand-Durasevic and D. Soll. 2004. Differential modes of transfer RNASer recognition in *Methanosarcina barkeri*. *J Biol Chem* 279(47): 48780-48786.

Kothe, U. and M. V. Rodnina. 2007. Codon reading by tRNAAla with modified uridine in the wobble position. *Mol Cell* 25(1): 167-174.

Kumar, R., L. Marechal-Drouard, K. Akama and I. Small. 1996. Striking differences in mitochondrial tRNA import between different plant species. *Mol Gen Genet* 252(4): 404-411.

Larkin, D.C., A. M. Williams, S. A. Martinis and G. E. Fox. 2002. Identification of essential domains for *Escherichia coli* tRNA(leu) aminoacylation and amino acid editing using minimalist RNA molecules. *Nucleic Acids Res* 30(10): 2103-2113.

Lartigue, C., J. I. Glass, N. Alperovich, R. Pieper, P. P. Parmar, C. A. Hutchison, 3rd, H. O, Smith and J. C. Venter. 2007. Genome transplantation in bacteria: changing one species to another. *Science* 317(5838): 632-638.

Lawther, R. P. and G. W. Hatfield. 1980. Multivalent translational control of transcription termination at attenuator of ilvGEDA operon of *Escherichia coli* K-12. *Proc Natl Acad Sci USA* 77(4): 1862-1866.

Leuker, C. E. and J. F. Ernst. 1994. Toxicity of a heterologous leucyl-tRNA (anticodon CAG) in the pathogen *Candida albicans*: in vivo evidence for non-standard decoding of CUG codons. *Mol Gen Genet* 245(2): 212-217.

Marck, C. and H. Grosjean. 2002. tRNomics: analysis of tRNA genes from 50 genomes of Eukarya, Archaea, and Bacteria reveals anticodon-sparing strategies and domain-specific features. *RNA* 8(10): 1189-1232.

Miranda, I., R. Silva and M. A. Santos. 2006. Evolution of the genetic code in yeasts. *Yeast* 23(3): 203-213.

Murakami, S., K. Kuehnle and D. B. Stern. 2005. A spontaneous tRNA suppressor of a mutation in the *Chlamydomonas reinhardtii* nuclear MCD1 gene required for stability of the chloroplast petD mRNA. *Nucleic Acids Res* 33(10): 3372-3380.

Nasvall, S. J., P. Chen and G. R. Bjork. 2004. The modified wobble nucleoside uridine-5-oxyacetic acid in tRNAPro (cmo5UGG) promotes reading of all four proline codons in vivo. *RNA* 10(10): 1662-1673.

Nasvall, S. J., P. Chen and G. R. Bjork. 2007. The wobble hypothesis revisited: uridine-5-oxyacetic acid is critical for reading of G-ending codons. *RNA* 13(12): 2151-2164.

Normanly, J., L. G. Kleina, J. M. Masson, J. Abelson and J. H. Miller. 1990. Construction of *Escherichia coli* amber suppressor tRNA genes. III. Determination of tRNA specificity. *J Mol Biol* 213(4): 719-726.

Normanly, J., R. C. Ogden, S. J. Horvath and J. Abelson. 1986. Changing the identity of a transfer RNA. *Nature* 321(6067): 213-219.

Normanly, J., T. Ollick and J. Abelson. 1992. Eight base changes are sufficient to convert a leucine-inserting tRNA into a serine-inserting tRNA. *Proc Natl Acad Sci USA* 89(12): 5680-5684.

Perry, J., X. Dai and Y. Zhao. 2005. A mutation in the anticodon of a single tRNAala is sufficient to confer auxin resistance in *Arabidopsis*. *Plant Physiol* 139(3): 1284-1290.

Qian, Q. and G. R. Bjork. 1997. Structural requirements for the formation of 1-methylguanosine in vivo in tRNA(Pro) GGG of *Salmonella typhimurium*. *J Mol Biol* 266(2): 283-296.

Redlak, M., C. Andraos-Selim, R. Giege, C. Florentz and W. M. Holmes. 1997. Interaction of tRNA with tRNA (guanosine-1)methyltransferase: binding specificity determinants involve the dinucleotide G36pG37 and tertiary structure. *Biochemistry* 36(29): 8699-8709.

Schultz, D. W. and M. Yarus. 1994. tRNA structure and ribosomal function. I. tRNA nucleotide 27-43 mutations enhance first position wobble. *J Mol Biol* 235(5): 1381-1394.

Schultz, D. W. and M. Yarus. 1994. tRNA structure and ribosomal function. II. Interaction between anticodon helix and other tRNA mutations. *J Mol Biol* 235(5): 1395-1405.

Shimizu, M., H. Asahara, K. Tamura, T. Hasegawa and H. Himeno. 1992. The role of anticodon bases and the discriminator nucleotide in the recognition of some *E. coli* tRNAs by their aminoacyl-tRNA synthetases. *J Mol Evol* 35(5): 436-443.

Small, I., L. Marechal-Drouard, J. Masson, G. Pelletier, A. Cosset, J. H. Weil and A. Dietrich. 1992. In vivo import of a normal or mutagenized heterologous transfer RNA into the mitochondria of transgenic plants: towards novel ways of influencing mitochondrial gene expression? *Embo J* 11(4): 1291-1296.

Smith, H. O., C. A. Hutchison, 3rd, C. Pfannkoch and J. C. Venter. 2003. Generating a synthetic genome by whole genome assembly: phiX174 bacteriophage from synthetic oligonucleotides. *Proc Natl Acad Sci USA* 100(26): 15440-15445.

Soma, A., R. Kumagai, K. Nishikawa and H. Himeno. 1996. The anticodon loop is a major identity determinant of *Saccharomyces cerevisiae* tRNA(Leu). *J Mol Biol* 263(5): 707-714.

Soma, A., K. Uchiyama, T. Sakamoto, M. Maeda and H. Himeno. 1999. Unique recognition style of tRNA(Leu) by Haloferax volcanii leucyl-tRNA synthetase. *J Mol Biol* 293(5): 1029-1038.

Sugiyama, H., M. Ohkuma, Y. Masuda, S. M. Park, A. Ohta and M. Takagi. 1995. In vivo evidence for non-universal usage of the codon CUG in *Candida maltosa*. *Yeast* 11(1): 43-52.

Tats, A., M. Remm and T. Tenson. 2006. Highly expressed proteins have an increased frequency of alanine in the second amino acid position. *BMC Genomics* 7: 28.

Tian, J., H. Gong, N. Sheng, X. Zhou, E. Gulari, X. Gao and G. Church. 2004. Accurate multiplex gene synthesis from programmable DNA microchips. *Nature* 432(7020): 1050-1054.

Tocchini-Valentini, G., M. E. Saks and J. Abelson. 2000. tRNA leucine identity and recognition sets. *J Mol Biol* 298(5): 779-793.

Tsang, T. H., M. Buck and B. N. Ames. 1983. Sequence specificity of tRNA-modifying enzymes. An analysis of 258 tRNA sequences. *Biochim Biophys Acta* 741(2): 180-196.

Wiltschi, B. and N. Budisa. 2007. Natural history and experimental evolution of the genetic code. *Appl Microbiol Biotechnol* 74(4): 739-753.

Yarus, M. 1982. Translational efficiency of transfer RNA's: uses of an extended anticodon. *Science* 218(4573): 646-652.

Zimmer, T. and W. H. Schunck. 1995. A deviation from the universal genetic code in *Candida maltosa* and consequences for heterologous expression of cytochromes P450 52A4 and 52A5 in *Saccharomyces cerevisiae*. *Yeast* 11(1): 33-41.

The invention claimed is:

1. A genetically engineered prokaryotic cell comprising a genome that comprises, compared to a corresponding wild-type prokaryotic cell having wild-type genetic code:
   (a) substitutions of all occurrences of at least two codons, in one or more protein-encoding sequences in the genome, with substituted codons that code for different amino acids according to the wild-type genetic code, and
   (b) alterations to tRNA genes such that the altered tRNA comprise anticodons cognate to unsubstituted codons but carry amino acids that the unsubstituted codons code for according to the wild-type genetic code,
   thereby the one or more protein-encoding sequence in the genetically engineered cell encodes the same amino acid sequence as the one or more protein-encoding sequence in the wild-type cell.

2. The cell of claim 1 wherein all occurrences of a first codon are substituted with a second codon and all occurrences of the second codon are substituted with the first codon.

3. The cell of claim 1 wherein all occurrences of codons coding for a first amino acid according to the wild-type genetic code are substituted with codons that code for a second amino acid according to the wild-type genetic code.

4. The cell of claim 1, wherein the alterations of the tRNA genes comprise substituting nucleotides at positions 1-26 and 44-76 of the tRNA with nucleotides at positions 1-26 and 44-76 from the tRNAs that carry amino acids that the unsubstituted codons code for according to the wild-type genetic code.

5. The cell of claim 1, wherein the alterations of the tRNA genes comprise substituting nucleotides at positions 1 through 26, 27, 28, 29, 30, 31, 32 or 33 and 37, 38, 39, 40, 41, 42, 43 or 44 through 76 of the tRNA with nucleotides at positions 1 through 26, 27, 28, 29, 30, 31, 32 or 33 and 37, 38, 39, 40, 41, 42, 43 or 44 through 76 from the tRNAs that carry amino acids that the unsubstituted codons code for according to the wild-type genetic code.

6. The cell of claim 1, wherein codons coding for serine are substituted with codons coding for leucine or alanine, both according to the wild-type genetic code.

7. The cell of claim 1, wherein codons coding for leucine are substituted with codons coding for serine or alanine, both according to the wild-type genetic code.

8. The cell of claim 1, wherein codons coding for alanine are substituted with codons coding for serine or leucine, both according to the wild-type genetic code.

9. The cell of claim 1, wherein codons coding for serine are substituted with codons coding for leucine or alanine, codons coding for leucine are substituted with codons coding for alanine or serine, and codons coding for alanine are substituted with codons coding for serine or leucine, all according to the wild-type genetic code.

10. The cell of claim 1, wherein the codon substitutions comprise one or more provided in Table 1.

11. An in vitro translation system derived from the cell of claim 1.

12. A method for preparing a genetically engineered prokaryotic cell, comprising:
   (i) preparing a genome that comprises, compared to a corresponding wild-type prokaryotic cell having wild-type genetic code:
      (a) substitutions of all occurrences of at least two codons, in one or more protein-encoding sequences in the genome, with substituted codons that code for different amino acids according to the wild-type genetic code, and
      (b) alterations to tRNA genes corresponding to the substituted codons such that the altered tRNA carry amino acids that the unsubstituted codons code for according to the wild-type genetic code,
      thereby the one or more protein-encoding sequence in the genetically engineered cell encodes the same amino acid sequence as the one or more protein-encoding sequence in the wild-type cell, and
   (ii) transformed the genome into a prokaryotic cell that does not contain genomic material.

13. The method of claim 12, wherein the alterations of the tRNA genes comprise substituting nucleotides at positions 1-26 and 44-76 of the tRNA with nucleotides at positions 1-26 and 44-76 from the tRNAs that carry amino acids that the unsubstituted codons code for according to the wild-type genetic code.

14. The method of claim 12, wherein the alterations of the tRNA genes comprise substituting nucleotides at positions 1 through 26, 27, 28, 29, 30, 31, 32 or 33 and 37, 38, 39, 40, 41, 42, 43 or 44 through 76 of the tRNA with nucleotides at positions 1 through 26, 27, 28, 29, 30, 31, 32 or 33 and 37, 38, 39, 40, 41, 42, 43 or 44 through 76 from the tRNAs that carry amino acids that the unsubstituted codons code for according to the wild-type genetic code.

15. The method of claim 12, wherein all occurrences of a first codon are substituted with a second codon and all occurrences of the second codon are substituted with the first codon.

16. The method of claim 12, wherein all occurrences of codons coding for a first amino acid according to the wild-type genetic code are substituted with codons that code for a second amino acid according to the wild-type.

17. The method of claim 12, wherein codons coding for serine are substituted with codons coding for leucine or alanine, both according to the wild-type genetic code.

18. The method of claim 12, wherein codons coding for leucine are substituted with codons coding for serine or alanine, both according to the wild-type genetic code.

19. The method of claim 12, wherein codons coding for alanine are substituted with codons coding for serine or leucine, both according to the wild-type genetic code.

20. The method of claim 12, wherein codons coding for serine are substituted with codons coding for leucine or alanine, codons coding for leucine are substituted with codons coding for alanine or serine, and codons coding for alanine are substituted with codons coding for serine or leucine, all according to the wild-type genetic code.

21. The method of claim 12, wherein the codon substitutions comprise one or more provided in Table 1.

\* \* \* \* \*

```
                          SEQUENCE LISTING

<160> NUMBER OF SEQ ID NOS: 8

<210> SEQ ID NO 1
<211> LENGTH: 87
<212> TYPE: RNA
<213> ORGANISM: Escherichia coli

<400> SEQUENCE: 1
gcgaaggugg cggaauuggu agacgcgcua gcuucaggug uuaguguucu uacggacgug      60
gggguucaag uccccccccu cgcacca                                         87

<210> SEQ ID NO 2
<211> LENGTH: 90
<212> TYPE: RNA
<213> ORGANISM: Escherichia coli

<400> SEQUENCE: 2
ggagagaugc cggagcggcu gaacggaccg gucucgaaaa ccggaguagg ggcaacucua      60
ccggggguuc aaaucccccu cucuccgcca                                      90

<210> SEQ ID NO 3
<211> LENGTH: 45
<212> TYPE: DNA
<213> ORGANISM: Escherichia coli

<400> SEQUENCE: 3
ggaagtgtgg ccgagcggtt gaaggcaccg gtcttgaaaa ccggc                     45

<210> SEQ ID NO 4
<211> LENGTH: 45
<212> TYPE: DNA
<213> ORGANISM: Escherichia coli

<400> SEQUENCE: 4
gcgggagtgg cgaaattggt agacgcacca gatttaggtt ctggc                     45

<210> SEQ ID NO 5
<211> LENGTH: 45
<212> TYPE: DNA
<213> ORGANISM: Escherichia coli

<400> SEQUENCE: 5
ggagagatgc cggagcggct gaacggaccg gtctcgaaaa ccgga                     45

<210> SEQ ID NO 6
<211> LENGTH: 45
```

```
<212> TYPE: DNA
<213> ORGANISM: Escherichia coli

<400> SEQUENCE: 6
gcgaaggtgg cggaattggt agacgcgcta gcttcaggtg ttagt            45

<210> SEQ ID NO 7
<211> LENGTH: 45
<212> TYPE: DNA
<213> ORGANISM: Escherichia coli

<400> SEQUENCE: 7
ggtgaggtgt ccgagtggct gaaggagcac gcctggaaag tgtgt            45

<210> SEQ ID NO 8
<211> LENGTH: 45
<212> TYPE: DNA
<213> ORGANISM: Escherichia coli

<400> SEQUENCE: 8
gccgaggtgg tggaattggt agacacgcta ccttgaggtg gtagt            45
```